(12) United States Patent
McHugo

(10) Patent No.: US 9,308,108 B2
(45) Date of Patent: Apr. 12, 2016

(54) CONTROLLED RELEASE AND RECAPTURE STENT-DEPLOYMENT DEVICE

(71) Applicant: Cook Medical Technologies LLC, Bloomington, IN (US)

(72) Inventor: Vincent McHugo, Co. Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 63 days.

(21) Appl. No.: 14/181,272

(22) Filed: Feb. 14, 2014

(65) Prior Publication Data

US 2015/0230954 A1   Aug. 20, 2015

Related U.S. Application Data

(60) Provisional application No. 61/779,373, filed on Mar. 13, 2013.

(51) Int. Cl.
*A61F 2/06* (2013.01)
*A61F 2/966* (2013.01)
*A61F 2/95* (2013.01)

(52) U.S. Cl.
CPC .......... *A61F 2/966* (2013.01); *A61F 2002/9517* (2013.01); *A61F 2002/9528* (2013.01)

(58) Field of Classification Search
CPC ... A61F 2/95; A61F 2/966; A61F 2002/9517; A61F 2002/9528; A61F 2002/9534; A61F 2002/9522; A61F 2/06
USPC ................................................ 623/1.11, 1.12
See application file for complete search history.

(56) References Cited

U.S. PATENT DOCUMENTS

| | | |
|---|---|---|
| 1,724,983 A | 8/1929 | Weiss |
| 3,132,549 A | 5/1964 | Lee |
| 3,888,258 A | 6/1975 | Akiyama |
| 3,897,786 A | 8/1975 | Garnett et al. |
| 4,559,041 A | 12/1985 | Razi |
| 4,655,771 A | 4/1987 | Wallsten |
| 4,921,484 A | 5/1990 | Hillstead |
| 5,026,377 A | 6/1991 | Burton et al. |
| 5,275,151 A | 1/1994 | Shockey et al. |
| 5,372,600 A | 12/1994 | Beyar et al. |

(Continued)

FOREIGN PATENT DOCUMENTS

| | | | |
|---|---|---|---|
| CA | 2739275 A1 | 4/2010 |
| EP | 566 807 A1 | 10/1993 |

(Continued)

OTHER PUBLICATIONS

Albee, F., "Bone Surgery with Machine Tools," Scientific American, Apr. 1936, pp. 178-181.

(Continued)

*Primary Examiner* — Victor Nguyen
(74) *Attorney, Agent, or Firm* — Brinks Gilson & Lione

(57) ABSTRACT

A delivery device for deploying and resheathing an expandable prosthesis such as a stent. The delivery device includes a movable outer sheath and a fixed pusher/holder member that are configured for the sheath to retract in a proximal direction to release and/or to extend distally to resheath the stent. The device includes a spring-tensioned anti-backlash mechanism to accommodate any backlash elongation and/or compression of the pusher/holder member and sheath.

12 Claims, 3 Drawing Sheets

(56) References Cited

U.S. PATENT DOCUMENTS

| | | |
|---|---|---|
| 5,415,664 A | 5/1995 | Pinchuk |
| 5,433,723 A | 7/1995 | Lindenberg et al. |
| 5,443,477 A | 8/1995 | Marin et al. |
| 5,458,615 A | 10/1995 | Klemm et al. |
| 5,554,894 A | 9/1996 | Sepielli |
| 5,681,323 A | 10/1997 | Arick |
| 5,683,451 A | 11/1997 | Lenker et al. |
| 5,690,644 A | 11/1997 | Yurek et al. |
| 5,700,269 A | 12/1997 | Pinchuk et al. |
| 5,702,418 A | 12/1997 | Ravenscroft |
| 5,707,376 A | 1/1998 | Kavteladze et al. |
| 5,709,703 A | 1/1998 | Lukic et al. |
| 5,733,325 A | 3/1998 | Robinson et al. |
| 5,759,186 A | 6/1998 | Bachmann et al. |
| 5,776,142 A | 7/1998 | Gunderson |
| 5,833,694 A | 11/1998 | Poncet |
| 5,906,619 A | 5/1999 | Olson et al. |
| 5,944,727 A | 8/1999 | Ahari et al. |
| 5,968,052 A | 10/1999 | Sullivan, III et al. |
| 5,993,460 A | 11/1999 | Beitelia et al. |
| 6,093,194 A | 7/2000 | Mikus et al. |
| 6,146,415 A | 11/2000 | Fitz |
| 6,162,231 A | 12/2000 | Mikus et al. |
| 6,168,610 B1 | 1/2001 | Marin et al. |
| 6,238,402 B1 | 5/2001 | Sullivan, III et al. |
| 6,254,628 B1 | 7/2001 | Wallace et al. |
| 6,346,118 B1 | 2/2002 | Baker et al. |
| 6,375,676 B1 | 4/2002 | Cox |
| 6,383,211 B1 | 5/2002 | Stachle |
| 6,391,050 B1 | 5/2002 | Broome |
| 6,391,051 B2 | 5/2002 | Sullivan, III et al. |
| 6,402,760 B1 | 6/2002 | Fedida |
| 6,413,269 B1 | 7/2002 | Bui et al. |
| 6,428,566 B1 | 8/2002 | Holt |
| 6,514,261 B1 | 2/2003 | Randall et al. |
| 6,520,983 B1 | 2/2003 | Colgan et al. |
| 6,530,949 B2 | 3/2003 | Konya et al. |
| 6,592,549 B2 | 7/2003 | Gerdts et al. |
| 6,599,296 B1 | 7/2003 | Gillick et al. |
| 6,629,981 B2 | 10/2003 | Bui et al. |
| 6,669,719 B2 | 12/2003 | Wallace et al. |
| 6,673,101 B1 | 1/2004 | Fitzgerald et al. |
| 6,695,862 B2 | 2/2004 | Cox et al. |
| 6,695,875 B2 | 2/2004 | Stelter et al. |
| 6,749,627 B2 | 6/2004 | Thompson et al. |
| 6,755,854 B2 | 6/2004 | Gillick et al. |
| 6,755,855 B2 | 6/2004 | Yurek et al. |
| 6,786,918 B1 | 9/2004 | Krivoruchko et al. |
| 6,808,529 B2 | 10/2004 | Fulkerson |
| 6,821,291 B2 | 11/2004 | Bolea et al. |
| 6,860,898 B2 | 3/2005 | Stack et al. |
| 6,866,669 B2 | 3/2005 | Buzzard et al. |
| 6,890,317 B2 | 5/2005 | Gerdts et al. |
| 6,893,458 B2 | 5/2005 | Cox et al. |
| 6,911,039 B2 | 6/2005 | Shiu et al. |
| 6,926,732 B2 | 8/2005 | Derus et al. |
| 6,939,352 B2 | 9/2005 | Buzzard et al. |
| 6,942,688 B2 | 9/2005 | Bartholf et al. |
| 6,991,646 B2 | 1/2006 | Clerc et al. |
| 7,052,511 B2 | 5/2006 | Weldon et al. |
| 7,122,058 B2 | 10/2006 | Levine et al. |
| 7,335,224 B2 | 2/2008 | Øhlenschlæger |
| 8,932,342 B2* | 1/2015 | McHugo et al. ............. 623/1.11 |
| 2002/0007206 A1 | 1/2002 | Bui et al. |
| 2002/0095203 A1 | 7/2002 | Thompson et al. |
| 2002/0111666 A1 | 8/2002 | Hart et al. |
| 2002/0183827 A1 | 12/2002 | Derus et al. |
| 2003/0093084 A1 | 5/2003 | Nissan et al. |
| 2003/0144671 A1 | 7/2003 | Brooks et al. |
| 2003/0191516 A1 | 10/2003 | Weldon et al. |
| 2003/0225445 A1 | 12/2003 | Derus et al. |
| 2004/0006380 A1 | 1/2004 | Buck et al. |
| 2004/0010265 A1 | 1/2004 | Karpiel |
| 2004/0093057 A1 | 5/2004 | Bolduc et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0215229 A1 | 10/2004 | Coyle |
| 2004/0220653 A1 | 11/2004 | Borg et al. |
| 2004/0267282 A1 | 12/2004 | Shkarubo et al. |
| 2005/0021123 A1 | 1/2005 | Dorn et al. |
| 2005/0033402 A1 | 2/2005 | Cully et al. |
| 2005/0033403 A1 | 2/2005 | Ward et al. |
| 2005/0060016 A1 | 3/2005 | Wu et al. |
| 2005/0060018 A1 | 3/2005 | Dittman |
| 2005/0080476 A1 | 4/2005 | Gunderson et al. |
| 2005/0085890 A1 | 4/2005 | Rasmussen et al. |
| 2005/0090834 A1 | 4/2005 | Chiang et al. |
| 2005/0090890 A1 | 4/2005 | Wu et al. |
| 2005/0107862 A1 | 5/2005 | Ohlenschlaeger |
| 2005/0113902 A1 | 5/2005 | Geiser et al. |
| 2005/0131514 A1 | 6/2005 | Hijlkema et al. |
| 2005/0149159 A1 | 7/2005 | Andreas et al. |
| 2005/0177246 A1 | 8/2005 | Datta et al. |
| 2005/0182475 A1 | 8/2005 | Jen et al. |
| 2005/0209670 A1 | 9/2005 | George et al. |
| 2005/0209685 A1 | 9/2005 | Shifrin et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0004433 A1 | 1/2006 | Greenberg et al. |
| 2006/0009858 A1 | 1/2006 | Levine et al. |
| 2006/0184224 A1 | 8/2006 | Angel |
| 2006/0184226 A1 | 8/2006 | Austin |
| 2007/0060996 A1 | 3/2007 | Goodin et al. |
| 2007/0060999 A1 | 3/2007 | Randall et al. |
| 2007/0219614 A1 | 9/2007 | Hartley |
| 2008/0300613 A1 | 12/2008 | Shelton, IV et al. |
| 2009/0024133 A1 | 1/2009 | Keady et al. |
| 2009/0030497 A1 | 1/2009 | Metcalf et al. |
| 2009/0099640 A1 | 4/2009 | Weng |
| 2010/0168834 A1 | 7/2010 | Ryan et al. |
| 2010/0262157 A1 | 10/2010 | Silver et al. |
| 2011/0190865 A1 | 8/2011 | McHugo et al. |
| 2012/0172963 A1 | 7/2012 | Ryan et al. |
| 2012/0221093 A1 | 8/2012 | McHugo |

FOREIGN PATENT DOCUMENTS

| | | |
|---|---|---|
| EP | 0747021 A2 | 12/1996 |
| EP | 1 525 859 A2 | 4/2005 |
| JP | 2005/532100 A | 10/2005 |
| JP | 2007/508069 A | 4/2007 |
| WO | WO 98/53761 A1 | 12/1998 |
| WO | WO 02/05885 A2 | 1/2002 |
| WO | WO 2005/107644 A1 | 11/2005 |
| WO | WO 2007/005799 A1 | 1/2007 |
| WO | WO 2007/022395 A1 | 2/2007 |
| WO | WO 2008/042266 A2 | 4/2008 |
| WO | WO 2009/012061 A1 | 1/2009 |
| WO | WO 2010/040009 A1 | 4/2010 |
| WO | WO 2010/078352 A1 | 7/2010 |
| WO | WO 2011/094527 A1 | 8/2011 |
| WO | WO 2012/099731 A1 | 7/2012 |
| WO | WO 2012/099732 A1 | 7/2012 |
| WO | WO 2012/118638 A1 | 9/2012 |

OTHER PUBLICATIONS

International Search Report and the Written Opinion No. for Intl. No. PCT/US2012/020597, date of mailing May 21, 2012, 13 pgs.

International Search Report and Written Opinion of the International Searching Authority for International Application No. PCT/US2008/069019, dated Oct. 17, 2008, 9 pages.

International Search Report and Written Opinion of the International Searching Authority for International Application No. PCT/US2009/069721, dated Feb. 19, 2010, 9 pages.

(56) References Cited

OTHER PUBLICATIONS

International Search Report and Written Opinion of the International Searching Authority for International Application No. PCT/US2011/022903, dated Mar. 24, 2011, 9 pages.
International Search Report and Written Opinion of the International Searching Authority for International Application No. PCT/US2012/025895, dated Jun. 6, 2012, 12 pages.
International Search Report for International Application No. PCT/US2012/020598, dated May 10, 2012, 4 pages.
Office action from co-pending U.S. Appl. No. 12/649,046, dated Apr. 5, 2013, 11 pages.
Office action from Japanese Application No. 2011-544591, dated Oct. 29, 2013, 5 pages.

* cited by examiner

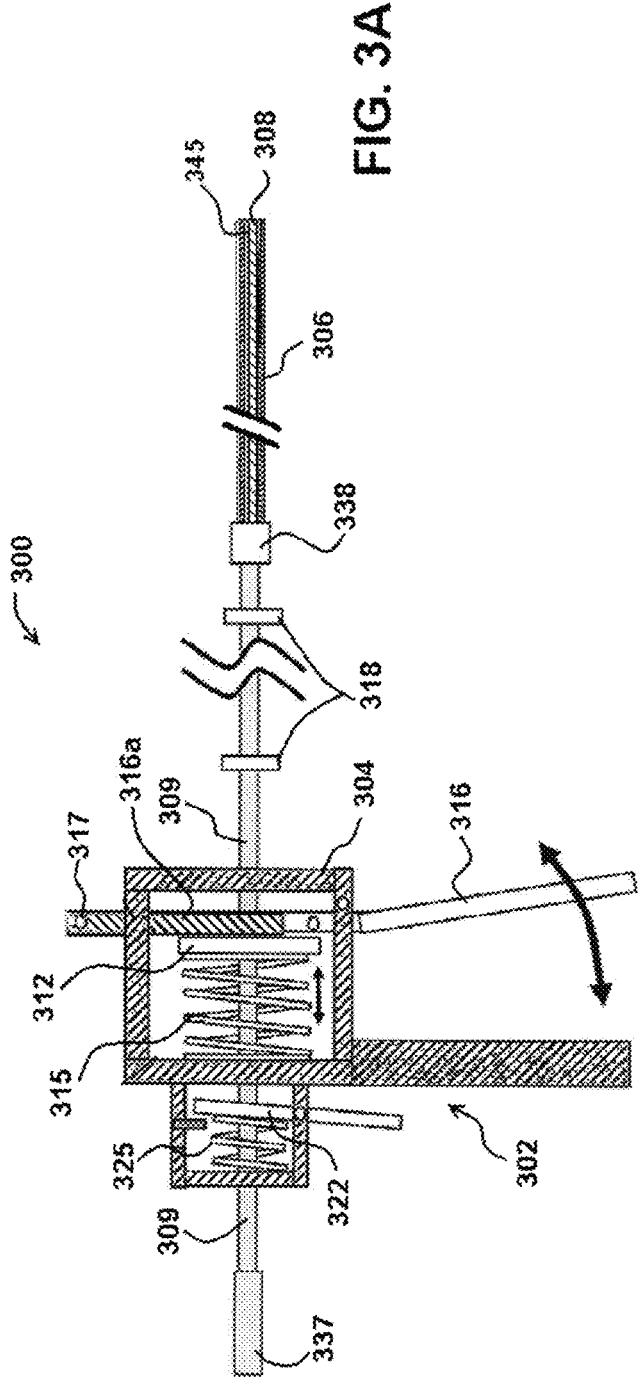
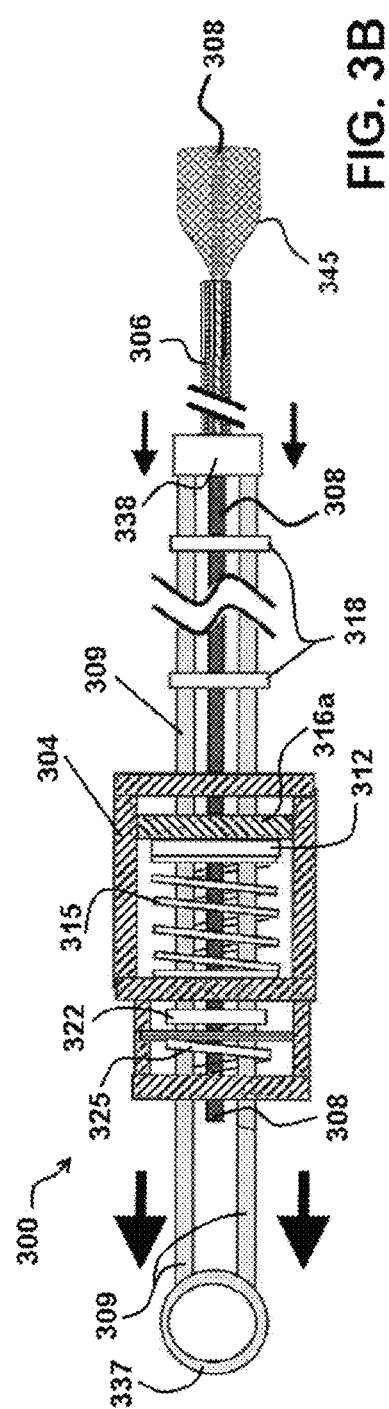
FIG. 3A
FIG. 3B

CONTROLLED RELEASE AND RECAPTURE STENT-DEPLOYMENT DEVICE

CROSS-REFERENCE TO RELATED APPLICATIONS

This application is a non-provisional application which claims priority to U.S. provisional application Ser. No. 61/179,373, filed Mar. 13, 2013, which is incorporated by reference herein in its entirety.

TECHNICAL FIELD

This invention relates to a medical device and, in particular to a delivery device for a self-expanding prosthesis and a method of delivering and deploying the prosthesis into a body lumen.

BACKGROUND

A self-expanding prosthesis such as a stent may be introduced into a patient's body using a delivery device that includes a push-pull mechanism with an outer catheter coaxially slidably disposed over an inner catheter. The prosthesis is disposed in a circumferentially-restrained configuration at the distal end of the device between the inner catheter and the outer catheter. The prosthesis may be deployed by proximally pulling back the outer catheter relative to the inner catheter, exposing the prosthesis and allowing it to deploy/circumferentially expand.

The push-pull delivery device described above may have several shortcomings. For example, when using this conventional push-pull delivery device, a physician may inadvertently retract the outer catheter too far and prematurely deploy the prosthesis in an incorrect position within a body lumen. In that circumstance, repositioning the prosthesis may be difficult, if not impossible, because the prosthesis already will have radially self-expanded and engaged the body lumen.

Accordingly, there is a need for a delivery system that can increase the control, accuracy and ease of placement during deployment of a prosthesis. The embodiments described below may be useful for increasing the control, accuracy and ease of placement during deployment of the prosthesis and may also solve other problems.

SUMMARY

Accordingly, a delivery device is provided including a fixed pusher member and a longitudinally-movable outer catheter sheath that is configured to retract/advance in proximal/distal directions for deploying and recapturing/resheathing an intraluminal prosthesis.

BRIEF DESCRIPTION OF THE DRAWINGS

Embodiments are described by way of example with reference to the accompanying drawings, in which:

FIGS. 3A-3B show a partial section view of another delivery device embodiment and method of use.

DETAILED DESCRIPTION OF THE PREFERRED EMBODIMENTS

Figure 1A:
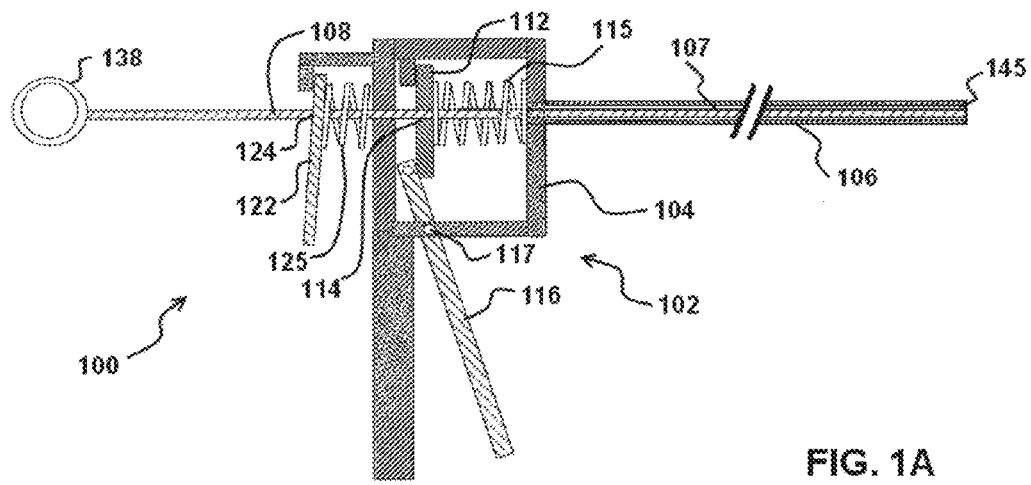
FIGS. 1A-1C show a partial section view of a delivery device embodiment and method of use.

The embodiments are described with reference to the drawings in which like elements are generally referred to by like numerals. The relationship and functioning of the various elements of the embodiments may be understood by reference to the drawings and the following detailed description. However, the embodiments described below are provided by way of example only, and the invention is not limited to the embodiments illustrated in the drawings. It should also be understood that the drawings are not to scale, and—in certain instances—details have been omitted that are not necessary for an understanding of the embodiments such as conventional details of fabrication and assembly.

Throughout the specification, the terms "distal" and "distally" shall denote a position, direction, or orientation that is generally away from the physician (including any other person holding/operating a device) and/or toward a treatment zone/patient. Accordingly, the terms "proximal" and "proximally" shall denote a position, direction, or orientation that is generally towards the physician. In FIGS. 1A-1C and 3A-3C, "distal" is generally to the right, and "proximal" is generally to the left. Various other constructions of deployment devices and methods may be understood with reference to U.S. Pat. App. Pub. Nos. 2012/0029607 and 2010/0168834, each of which is incorporated by reference herein in its entirety. Those of skill in the art will appreciate, with reference to the present disclosure, the novel ways in which the presently described structures may be used with the stent deployment devices and methods disclosed therein.

Referring now to the drawings in FIGS. 1A-3B, embodiments of a delivery device for deploying a self-expanding prosthesis are shown. As will be discussed, the delivery device is configured with the ability to resheath and reposition the prosthesis, thereby substantially increasing the control and accuracy of a deployment process as compared with conventional delivery devices.

Figure 1B:
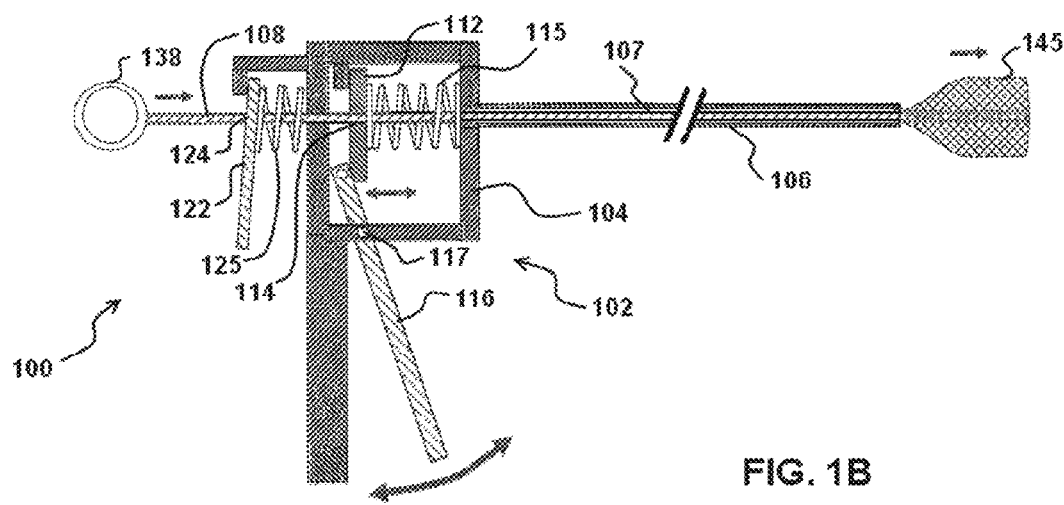
Figure 1C:
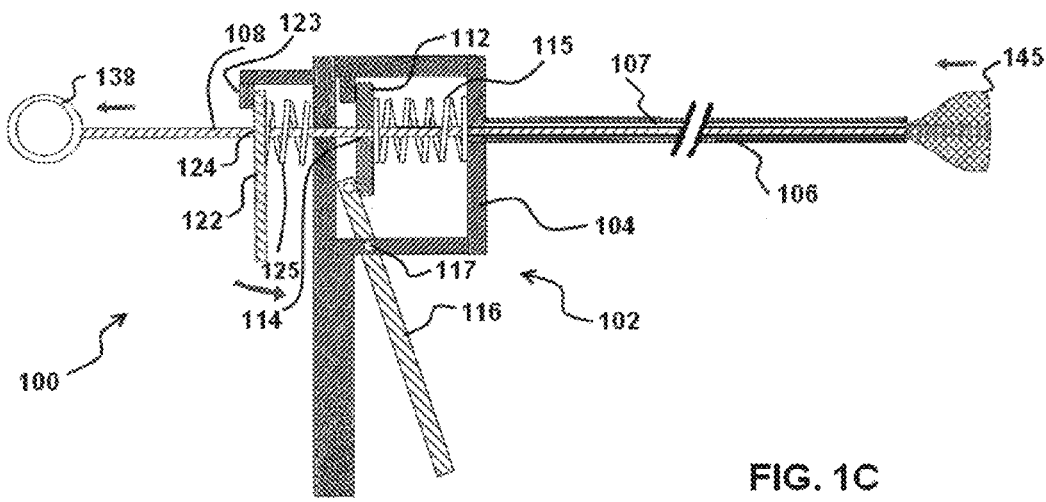

FIGS. 1A-1C show one embodiment of a delivery device 100, with reference to a method of use. The delivery device 100 includes a handle 102 with a handle body 104 and an elongate tubular sheath 106 fixedly attached to and extending distally from the handle body 104. An elongate pusher member 108 extends slidably through a longitudinal lumen 107 of the sheath 106. The handle body 104 is shown in a longitudinal cutaway view revealing the internal components of the handle 102.

The interior of the handle 102 includes an advancement plate member 112 that is biased toward the proximal end of the pusher member 108. In this embodiment, the advancement member 112 is shown as being biased by a coil spring 115, but other biasing means known in the art may be used. The advancement member 112 includes an advancement member aperture 114 through its thickness, through which the pusher member 108 extends. A trigger member 116 is pivotably mounted to the handle body 104 and is connected to or otherwise disposed in operative contact with the advancement member 112. When the pivot axis 117 is configured as shown, pivoting the lower portion of the trigger member 116 proximally toward the handle body 104 will pivot the upper portion of the trigger member 116 distally, pushing the advancement member 112 distally. When advanced distally by motivation from the trigger member 116, the advancement member 112 engages (in the manner described below with reference to FIGS. 2A-2B) and pushes distally the pusher member 108.

A keeper plate member 122 is also mounted to the handle body 104 and biased toward its proximal end against a keeper stop 123. In this embodiment, the keeper member 122 is shown as being biased by a coil spring 125, but other biasing means known in the art may be used. The keeper member 122 includes a keeper member aperture 124 through its thickness, through which the pusher member 108 extends. The keeper member functions as a "parking brake" or retaining means that will prevent proximal movement of the pusher member 108 when engaged thereto. This may be needed because, as a stent is deployed distally, the sheath 106 may stretch distally and then—when attempting to relax and return to its original length—it may introduce backlash that would drive the pusher 108 proximally if it weren't held in place.

The proximal end of the pusher member 108 may include a handle or other grasping portion such as a ring 138 that will facilitate a user grasping the pusher member 108 and moving it proximally and/or distally (albeit in a generally less controlled fashion than by employing the advancement and keeper/retractor members 112, 122). A distal portion of the pusher member 108 is attached to an expandable prosthesis such as, for example, an intraluminal device embodied as a self-expanding stent 145 (which, because it is sheathed in lumen 107 is not clearly visible in FIG. 1A). The stent 145 may be constrained by this attachment and/or by the sheath 106. In certain embodiments, the sheath and pusher member will be sufficiently flexible and elongate to introduce a prosthetic device into a patient's alimentary canal. For example, the device 100 may be used to introduce a stent into a patient's esophagus (e.g., via the patient's mouth) or along an intestinal lumen. Device embodiments may be used through natural and/or surgically-created orifices, and may be practiced on a scale suitable for vascular stenting. It should be appreciated that the self-expanding prosthesis may include one or more stents such as, for example, in a stent-graft structure that includes one or more stents supporting graft material.

Figure 2A:
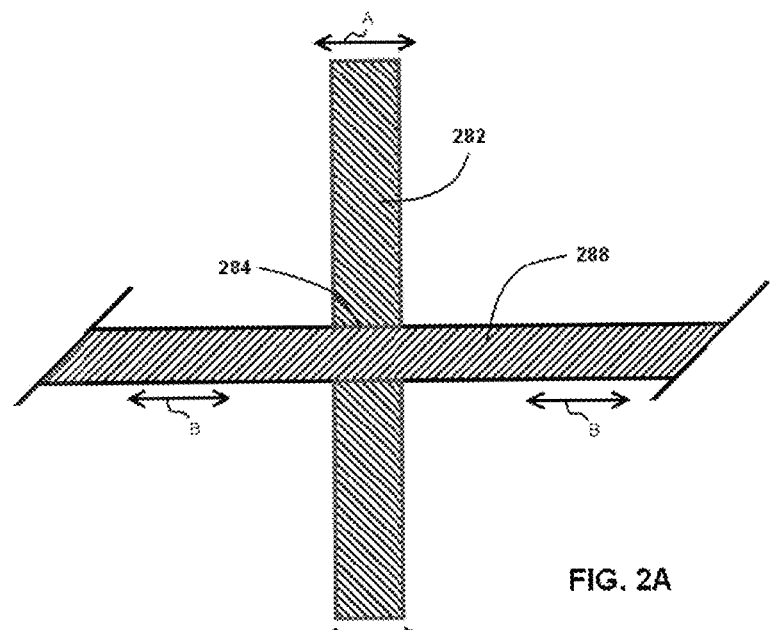
FIGS. 2A-2B show a diagrammatic section view of plate/pusher member interaction.
Figure 2B:
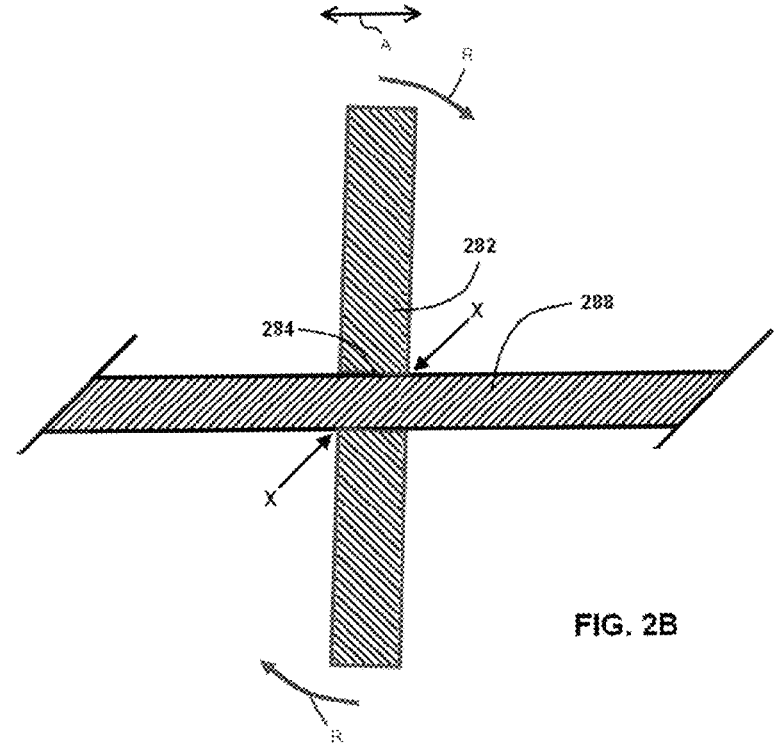

FIGS. 2A-2B illustrate the principle of operation of the attachment member 112 and the keeper member 122 with pusher member 108 (as well as analogous components of the other embodiments herein). The operation is described with reference to an apertured locking/gripping plate 282 (analogous to those members 112, 122, which function in the same manner) and a through-rod 288 (analogous to the pusher member 108, which functions in the same manner). The locking plate 282 includes an aperture 284 through its thickness. The inner diameter of the aperture 284 is preferably about the same or somewhat greater than an outer diameter of the through-rod 288.

As shown in FIG. 2A, when the long axis of the through-rod 288 is fully or nearly parallel or coaxial with the long axis of the aperture 284, the through-rod 288 can pass freely along its longitudinal axis through the aperture 284 (as indicated by linear motion arrows B), and/or the plate 282 may move freely along a length of the rod 288 (as indicated by linear motion arrows A). However, as shown in FIG. 2B, when the long axis of the aperture 284 is inclined at a sufficient angle relative to the long axis of the through-rod 288 (indicated by rotary motion arrows R), the border of the aperture grips, captures, binds, and/or otherwise engages an exterior surface of the through-rod 288 (e.g., in the regions indicated by designator arrows X), preferably with sufficient force to substantially or completely prevent the through-rod 288 from moving longitudinally relative to the locking plate 282.

In other words, when the aperture 284 is perpendicular to the long axis of the locking plate 282, the through-rod 288 can move freely therethrough when it is perpendicular to the locking plate 282, but will be engaged by the aperture when it is at a non-perpendicular angle relative to the locking plate. In the embodiments described here, the relative angle of a locking plate/keeper member to a through-rod/pusher member is also controlled by a spring-biased angle of the locking plate/keeper member. Those of skill in the art will appreciate from the figures that such an arrangement will allow free movement in one direction as contact/friction between the through-rod/pusher member and aperture of the locking plate/keeper member in one direction will move them generally perpendicular relative to each other, while movement in the opposite direction will angle them non-perpendicularly and thereby lock them together. Similarly, when the locking plate 282 is functioning as an advancement member (e.g., advancement member 112), the plate 282 may be angled to engage the rod 288 and then pushed in a direction coaxial with the rod's long axis such that the plate 282 will move the rod in the direction the plate is moved.

The external geometry of the through-rod 288 and the aperture 284 do not need to be the same (e.g., the aperture may be—for example—hexagonal, square, or circular, while the cross-sectional geometry of the through-rod may be—for example—elliptical, triangular, or pentagonal). This type of securement is well-known in the art and those of skill in the art will appreciate that various shapes of apertures and/or through-rods may be used within the scope of the present invention, including that the through-rod may be notched or otherwise frictionally-enhanced.

FIG. 1A shows the device 100 in an unactuated state, with the stent 145 being sheathed. Actuation of the device 100 with stent deployment is described with reference to FIG. 1B. To actuate the device 100 and advance the pusher member 108 distally, a user will pivot the lower portion of the trigger 116 toward the handle body 104. This action inclines the advancement member 112 to a first angle where its aperture captures/engages the pusher member 108 and pushes it forward/distally. During this action, the keeper member 122 is disposed at an angle wherein its aperture 124 allows freely sliding distal-ward passage of the pusher member 108 therethrough. When the trigger 116 is released, the proximal bias of the advancement member 112 moves it back to the default position shown in FIG. 1A. At the same time, the proximal bias of the keeper member 122 generally retains it in the default position shown in FIG. 1A. Serial actuation of the trigger 116 will advance the pusher member 108 and overlying stent 145 distally out of the distal end of the sheath 106 as shown in FIG. 1B.

During deployment of a stent 145 (e.g., into a patient's esophagus), it may be desirable or even needful to reposition the stent longitudinally or otherwise. When the stent 145 has been partially deployed such that it has expanded sufficiently to engage patient tissue, it may be difficult or impossible to move the stent longitudinally and/or rotationally without injuring the patient and/or damaging the stent if it remains expanded. The present device 100 provides for a resheathing function, described with reference to FIG. 1C. As is known in the art, the stent 145 and deployment device 100 may be visualized during a stent-placement procedure by ultrasound and/or fluoroscopy (e.g., based upon the construction of the stent and/or inclusion of specific markers such as echogenic and/or radio-opaque markers included in/on the stent, the device, or any combination thereof). Such visualization, which may also be done using a camera-type device (e.g., optical or electronic endoscope), will enable a physician to monitor and carefully control deployment and—if needed—resheathing/recapture of an expandable prosthesis such as a stent, stent-graft, or other prosthetic device.

If, during deployment, it becomes desirable to partially or completely resheath the stent 145, thereby reducing its outer diameter sufficiently to allow it to be repositioned without damaging the stent or surrounding tissue, a user may actuate (i.e., disengage the brake function of) the keeper member 122 by moving it to an angle generally perpendicular to the pusher member 108, which will release the pusher 108 and allow it to be moved proximally by the user pulling proximally on the loop 138.

In another aspect, the keeper 122 may function as a resheathing trigger. To actuate the keeper 122 in its function as a resheathing trigger and thereby retract the pusher member 108 proximally, a user will pivot the lower portion of the keeper 122 toward the handle body 104 sufficiently to release its engagement with the pusher 108 and then slide the keeper member 122 distally along the pusher 108. When it contacts the handle body 104, the user may then allow the keeper 122 to incline back to a first angle where its aperture captures/engages the pusher member 108 and pulls it (pusher 108) back/proximally (or, more accurately, is pushed back proximally by the bias of the spring 125). Specifically, when the keeper 122 is released, its proximal bias moves it back to the default position shown in FIG. 1A.

The proximal bias of the advancement member 112 by spring 115 generally retains it in the default position shown in FIG. 1A, disposed at an angle wherein its aperture 114 allows freely sliding distal-ward passage of the pusher member 108 therethrough. The device may be constructed such that serial actuation of the keeper 122 will retract the pusher member 108 and overlying stent 145 proximally back into the distal end of the sheath 106 as shown in FIG. 1C, which shows the stent 145 having been partially resheathed. Thereafter, the longitudinal position of the device 100 (with the sheathed stent 145) may be adjusted as desired, and the stent deployed as desired, in the manner described above with reference to FIGS. 1A-1B.

FIGS. 3A-3B show another embodiment of a delivery device 300, with reference to a method of use. The delivery device 300 includes a handle 302 with a handle body 304 and an elongate tubular sheath 306 fixedly attached to and extending distally from a sheath-attached puller 338 that extends slidably through the handle body 304. An elongate pusher/holder member 308 extends slidably through a longitudinal lumen 307 of the sheath 306, but is fixed relative to the handle body 304. The handle body 304 is shown in FIG. 3A in a side view revealing internal components of the handle 302. FIG. 3B shows a top view of the device 300 of FIG. 3A, with the sheath-attached puller 338 having been retracted proximally to actuate the device and release a distal portion of the stent 345.

The interior of the handle 302 includes an advancement plate member (also functioning as a retaining member) 312 that is biased toward the distal end of the stent-holder member 308. In this embodiment, the retaining member 312 is shown as being biased distally by a coil spring 315, but other biasing means known in the art may be used. The retaining member 312 is longitudinally freely movable along/relative to the holder member 308 and to the sheath-attached puller 309. A deployment/advancement trigger member 316 is pivotably mounted to the handle body 304 and the portion 316a of it inside the handle body 304 is contacted by the retaining member 312. That body-internal trigger portion 316a moves freely relative to the inner holder member 308 and is configured to engage the sheath-attached puller 309 only during a proximal stroke, but to reciprocate freely back to the more distal position shown in FIG. 3A when released and moved back to that position by the bias of the spring 315. Alternatively, or in addition, the retaining member 312 may engage the sheath-attached pulling member only when being moved proximally to pull it back upon actuation of the trigger 316, then freely reciprocate distally back along it to the position shown in FIG. 3A. When the pivot axis 317 is configured as shown, a user pivoting the lower portion of the trigger member 316 proximally will pull the retaining member 312 and the sheath-attached puller 309 both proximally. The advancement/retainer member 312 includes two apertures (not shown) through which the puller 309 passes.

A keeper member 322 (which serves also to accommodate and prevent any backlash introduced by stretching and/or compression of the holder member 308) is mounted within an upper portion of the handle body 304 and biased toward its distal end. In this embodiment, the keeper member 322 is shown as being biased by a distally/pushing-tensioned coil spring 325, but other biasing means known in the art may be used. The pusher member 308 extends through the keeper member 322 without being bound thereto. The keeper member 322 is also in mechanical communication with the sheath-attached puller 309, and—unless the keeper member 322 is rotated against its spring-bias—it contacts the sheath-attached puller 309 in a manner that prevents distal motion of the sheath-attached puller 309.

A distal portion of the pusher/holder member 308 is attached to or otherwise in releasable contact with an expandable prosthesis such as, for example, a self-expanding stent 345. The attachment may include one or more an abutment, attachment with wire(s) or the like, the stent being concentrically constricted around the member 308, or any other means. The stent 345 may be constrained by this attachment and/or by the sheath 306. A variety of methods and constructions are known and are being developed in the art for providing stent attachment and deployment from a central pusher member whether or not it is accompanied by an outer sheath. Many of these constructions and methods may be practiced in a useful manner within the scope of the present invention, one advantage of which is generally a more compact construction than other devices configured to perform the same or similar functions. One or more stabilizer elements 318 may be provided, attaching the sheath-attached puller member 309 slidably to the holder member 308. Although the stent-holder member 308 is longitudinally fixed relative to the handle body 304, the sheath 306 (which coaxially surrounds a distal length of the holder 308) is longitudinally slidable relative to the holder 308.

FIG. 3A shows the device 300 in an unactuated state, with the stent 345 being sheathed (and therefore not clearly visible in FIG. 3A). Actuation is described with reference to the top view of FIG. 3B. To actuate the device 300 and retract the sheath 306 proximally, a user will pivot the lower portion of the deployment trigger 316 toward the downward extending portion of the handle body 304. This action captures/engages the sheath-attached puller member 309 and pulls it proximally. One advantage of this embodiment is that such actuation can be completed with only one hand, which will provide clear advantages to treatment personnel using the device. Another advantage of this embodiment is that the handle remains in a fixed position relative to the expandable member 345 and relative to the patient's body (i.e., only the sheath moves longitudinally during actuation). During this action, the keeper member 322 is disposed at an angle wherein it allows freely sliding distal-ward passage of the sheath-attached puller member 309 therethrough. When the deployment trigger 316 is released, the distal bias of the retaining member 312 against the in-handle portion 316a of the trigger 316 moves it back to the default position shown in FIG. 3A. At the same time, the distal bias of the keeper member 322 generally retains it in the default position shown in FIG. 3A without retracting the pusher member 308. In this manner, it functions as a "parking brake" preventing undesired motion due to backlash in system components. Serial actuation of the deployment trigger 316 will retract the sheath-attached puller member 309 and release the stent 345 distally out of the distal end of the sheath 306 as shown in FIG. 3B.

Those of skill in the art will appreciate, with reference to the present disclosure, that the embodiment of FIGS. 3A-3B may be manually/directly actuated by depressing both the trigger 316 and the keeper member 322. (However, neither element may need to be actuated in practice to effect deployment.) Then, the proximal-end ring 337 of the sheath-attached puller member 309 can be pulled to retract the sheath and deploy the stent 345. The central pusher/holder member 308 may be constructed as a catheter including one or more lumens configured to allow passage of, for example, a wire guide, contrast fluid, or other useful tools or materials. The sheath 306 and pusher/holder member 308 are dimensioned and are sufficiently flexible and elongate to introduce a prosthetic device such as a stent into a patient's alimentary canal. The trigger 316 and keeper 322 can also be actuated in a manner allowing the sheath-attached puller member 309 to be advanced distally to re-sheath a partially-unsheathed stent 345 to allow for repositioning, if needed. Those of skill in the art will also appreciate that the present configuration for use with a "pistol grip"/"power grip" may readily be modified within the scope of the present disclosure to implement with use of an "internal precision grip."

The above figures and disclosure are intended to be illustrative and not exhaustive. This description will suggest to one of ordinary skill in the art many variations and alternatives that may be practiced within the scope of the present invention, including that many features described herein may be used in other embodiments described. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention. The scope of the present invention is defined by the claims directed thereto.

I claim:

1. A controlled release and recapture prosthetic deployment device comprising:
   a handle including a handle body;
   a tubular sheath;
   a sheath-attached puller extending slidably through the handle body and fixedly attached to the sheath; and
   an elongate stent-holder member fixedly extending through and distally out from the handle body, and further extending through a longitudinal lumen of the sheath, which sheath is slidable relative to the stent-holder member;
   wherein the handle comprises:
      a retaining member in the handle body, where the retaining member is biased toward a distal end of the device;
      a keeper member in the handle body, where the keeper body releasably engages the sheath-attached puller and is also biased toward the distal end of the device; and
      a first trigger member,
         pivotable relative to the handle body,
         disposed in mechanical communication with the retaining member, and
         configured to move the retaining member and the sheath-attached puller proximally when the trigger member is pivoted in a first direction.

2. The device of claim 1, further comprising a self-expanding prosthesis removably disposed within a distal portion of the sheath and attached to the holder member.

3. The device of claim 2, where the self-expanding prosthesis comprises a stent.

4. The device of claim 2, where the self-expanding prosthesis comprises a stent graft.

5. The device of claim 1, wherein the sheath-attached puller includes a proximal graspable structure configured for manual direct proximal retraction of the puller.

6. The device of claim 1, further comprising at least one stabilizer element connected to the sheath-attached puller and the holder member.

7. The device of claim 1, further comprising a self-expanding prosthesis removably disposed within a distal portion of the sheath, and configured wherein actuation of the trigger member moves the sheath proximally relative to the prosthesis, releasing the prosthesis from constraint by the sheath.

8. The device of claim 1, wherein the sheath and holder member are sufficiently flexible and elongate to introduce a prosthetic device into a patient's alimentary canal.

9. The device of claim 8, wherein the sheath and holder member are sufficiently flexible and elongate to introduce a prosthetic device into a patient's esophagus via the patient's mouth.

10. The device of claim 1, where the keeper body is also biased toward the distal device end by a spring.

11. The device of claim 1, where the keeper member includes a second trigger portion attached pivotably to the handle body.

12. The device of claim 1, where the handle body is configured for use with a power grip.

* * * * *